(12) United States Patent
Mennen

(10) Patent No.: US 7,622,609 B2
(45) Date of Patent: Nov. 24, 2009

(54) PROCESS FOR THE PREPARATION OF UREA

(75) Inventor: Johannes Henricus Mennen, Meijel (NL)

(73) Assignee: DSM IP Assets B.V., Heerlen (NL)

( * ) Notice: Subject to any disclaimer, the term of this patent is extended or adjusted under 35 U.S.C. 154(b) by 494 days.

(21) Appl. No.: 11/631,289

(22) PCT Filed: Jun. 6, 2005

(86) PCT No.: PCT/NL2005/000408

§ 371 (c)(1),
(2), (4) Date: Jan. 3, 2007

(87) PCT Pub. No.: WO2006/004395

PCT Pub. Date: Jan. 12, 2006

(65) Prior Publication Data

US 2008/0300422 A1    Dec. 4, 2008

(30) Foreign Application Priority Data

Jul. 7, 2004  (NL) ................................... 1026607

(51) Int. Cl.
*C07C 273/04* (2006.01)

(52) U.S. Cl. .............................. 564/67; 564/70; 564/71; 564/72

(58) Field of Classification Search ................... 564/67, 564/70, 71, 72
See application file for complete search history.

(56) References Cited

FOREIGN PATENT DOCUMENTS

| NL | 8 900 152 | 8/1990 |
|---|---|---|
| WO | WO 02/090323 | 11/2002 |
| WO | WO 03/087043 | 10/2003 |

OTHER PUBLICATIONS

International Search Report mailed Jul. 28, 2005 in PCT/NL2005/000408.
Written Opinion mailed Jul. 28, 2005 in PCT/NL2005/000408.

*Primary Examiner*—Peter G O'Sullivan
(74) *Attorney, Agent, or Firm*—Nixon & Vanderhye P.C.

(57) ABSTRACT

The invention relates to a process for the preparation of urea from ammonia and carbon dioxide in a urea plant that contains a high-pressure synthesis section and one or more recovery section(s) at a lower pressure, the high-pressure synthesis section comprising a reactor, a stripper and a condenser, with gases leaving the high-pressure synthesis section being condensed in a medium-pressure condenser at 0.5-12 MPa to which also a carbamate stream from one of the recovery sections is supplied, after which at least a part of the formed condensate is supplied to the high-pressure condenser.

16 Claims, 3 Drawing Sheets

PROCESS FOR THE PREPARATION OF UREA

Figure 1:
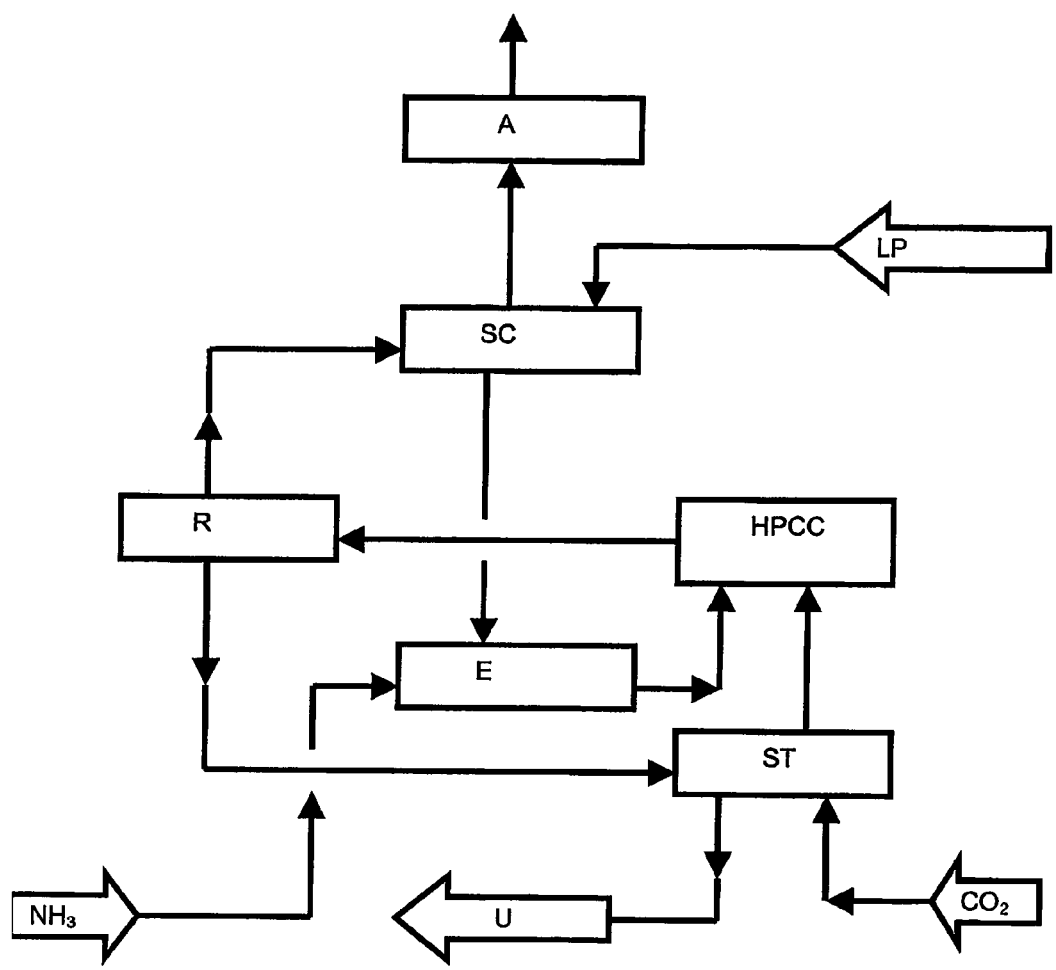

This application is the US national phase of international application PCT/NL2005/000408 filed 6 Jun. 2005 which designated the U.S. and claims benefit of NL 1026607, dated 7 Jul. 2004, the entire content of which is hereby incorporated by reference.

The invention relates to a process for the preparation of urea from ammonia and carbon dioxide in a urea plant containing a high-pressure synthesis section and a low-pressure recovery section, the high-pressure synthesis section comprising a reactor, a stripper and a condenser.

Urea plants are designed for a certain capacity. As a rule it is only to a limited extent possible to increase the capacity of an existing urea plant by increasing the amounts of starting materials and increasing the throughput of process streams. If it is desired to increase the capacity of a plant by increasing the throughput of the process streams, then it should be ensured that good efficiencies are achieved with the increased process streams in the various process steps. This holds in particular for the process steps that are carried out in the high-pressure part of the urea plant.

The high-pressure part of a urea plant substantially consists of a reactor in which the urea synthesis solution is prepared, a stripper in which the urea synthesis solution is stripped in countercurrent with one of the raw materials and/or heat, a condenser in which the gases released in the stripper are condensed and, in certain processes, a scrubber in which ammonia and carbon dioxide are removed from the synthesis gas.

Upon a capacity increase, bottlenecks in this high-pressure part may in particular be the stripping treatment of the urea synthesis solution in the stripper and the condensation in the condenser of the gases obtained in the stripping operation. The reason for this is that, if the liquid load of the stripping zone is raised too much, the stripping effect is largely lost due to, among other things, flooding. Flooding means that the liquid film inside the tubes in the stripper is broken down and part of the liquid is entrained by the exiting gas stream. This strongly reduces the stripping efficiency. The increase in the amounts of starting materials has little effect on the capacity of the reactor. The shorter residence time resulting from the higher throughput does have as a consequence that the ammonium carbamate content of the urea synthesis solution increases somewhat, so that more steam is needed in the stripper for decomposition of the ammonium carbamate. It is, therefore, the stripper that is the limiting factor rather than the reactor.

It should remain possible for the heat released upon condensation in the condenser of the gas mixture obtained In the stripping operation to be converted into usable steam using the existing heat-exchanging area, also at the increased gas mixture feed. Usable steam is understood to be saturated steam having a sufficiently high pressure for use in the recovery and concentration section(s) of the urea plant. It is found, however, that an increased feed of gas to be condensed, caused by the capacity increase, results in a too low steam pressure, as a consequence of which this steam can no longer be used for the purposes mentioned above within the urea process.

Said bottlenecks are largely the cause that it is only to a limited extent possible to expand the capacity of an existing plant without modification or replacement of expensive high-pressure equipment.

NL-A-8900152 and WO 02/090323 disclose processes for the preparation of urea in which it is possible to increase the capacity of a urea plant operating according to a stripping process without modifications being required in the high-pressure part of the urea synthesis.

This is achieved by preparing urea according to a process in which a urea synthesis solution is formed from carbon dioxide and ammonia in a reactor, with a part of the urea synthesis solution being transferred to a medium-pressure treatment zone. In this medium-pressure treatment zone this urea synthesis solution is contacted with an amount of carbon dioxide. The gas mixture formed in this medium-pressure treatment zone is subsequently condensed at medium pressure in a medium-pressure condensation zone. In NL-A-8900152 the residual urea synthesis solution leaving the medium-pressure treatment zone is transferred to a low-pressure recovery section, where the ammonium carbamate still present is largely decomposed and the gas mixture formed is separated. In WO-02/090323 the residual urea synthesis solution is transferred to the high-pressure scrubber.

A drawback of the above processes is that the medium-pressure section that is added should be fairly large to achieve a urea plant capacity extension of 25-40%.

In both cases the medium-pressure section comprises a dissociator, a stripper and a condenser.

The aim of the invention is to achieve the capacity expansion of the urea plant without having to modify the high-pressure part of the urea plant and with a simpler design of the medium-pressure section.

Surprisingly, it has now been found possible to increase the capacity of a urea plant without any modifications being required in the high-pressure section of the urea plant and with the medium-pressure section comprising only one or two items of equipment.

The invention is characterized in that gases leaving the high-pressure synthesis section are condensed in a medium-pressure condenser at 0.5-12 MPa to which also a carbamate stream from one of the recovery sections is supplied, following which at least a part of the condensate formed is supplied to the high-pressure condenser.

This way it is ensured that the condensation capacity in the urea plant is raised without the high-pressure condenser having to be enlarged, as a result of which a 20-40% capacity increase can be achieved. A second advantage is that due to the use of carbamate from one of the recovery sections during the condensation at medium pressure no additional water is supplied to the high-pressure section, so that the urea conversion in the reactor is comparable to the conversion in the reactor before the capacity increase.

A third advantage is that, since the medium-pressure section contains only the medium-pressure condenser, the investment required for the urea plant's capacity extension is low.

A fourth advantage is that the installation of the medium-pressure condenser makes it possible to control the steam pressure of the low-pressure steam formed in the high-pressure condenser at any desired level. This is important as a certain minimum steam pressure is needed to be able to use this steam in the lower-pressure section(s) of the urea plant.

The invention relates to a process for the preparation of urea from ammonia and carbon dioxide in a urea plant that contains a high-pressure synthesis section and one or more recovery section(s) operating at lower pressure. The high-pressure section usually operates at a pressure between 12 and 40 MPa. A urea plant normally comprises in any case one recovery section operating at low pressure, this being a pressure between 0.1 and 0.4 MPa. In some embodiments the urea plant may also comprise a medium-pressure recovery section operating at a pressure between 0.5 and 4 MPa.

The high-pressure synthesis section comprises a reactor, a stripper, a condenser and optionally a scrubber. A high-pressure scrubber is for instance present if the preparation of urea takes place according to the $CO_2$ stripping process or the ACES21 process.

Urea can be prepared by introducing excess ammonia together with carbon dioxide into a reactor at a high pressure and elevated temperature (for example 160-250° C.), which first results in the formation of ammonium carbamate according to the reaction:

$$2NH_3 + CO_2 \rightarrow H_2N-CO-ONH_4$$

Dehydration of the ammonium carbamate formed then results in the formation of urea according to the equilibrium reaction:

$$H_2N-CO-ONH_4 \leftrightharpoons H_2N-CO-NH_2 + H_2O$$

The theoretical maximum conversion of ammonia and carbon dioxide into urea is determined by the thermodynamic position of the equilibrium and depends on, for example, the $NH_3/CO_2$ ratio (N/C ratio), the $H_2O/CO_2$ ratio (H/C ratio) and the temperature. From the above reaction equations it can be deduced that the use of an excess of water in the reactor has a negative effect on the theoretical maximum conversion.

The reactor may consist of separate zones for the formation of ammonium carbamate and urea. These zones may be combined in one apparatus. The synthesis may be carried out in one or two reactors. When use is made of two reactors, the first reactor may for example be operated using virtually fresh raw materials and the second one using raw materials that are obtained entirely or partly elsewhere in the process that are recycled to the reactor.

The conversion of ammonium carbamate into urea and water in the reactor can be effected by ensuring a sufficiently long residence time of the reaction mixture in this zone. The residence time will generally be longer than 10 minutes, preferably longer than 20 minutes. The residence time will generally be shorter than 3 hours, preferably shorter than 1 hour.

During the conversion of ammonia and carbon dioxide into urea in the reactor a urea synthesis solution is obtained as a reaction product which consists essentially of urea, water, ammonium carbamate and unbound ammonia. Besides a urea synthesis solution, in the reactor also a gas mixture of unconverted ammonia and carbon dioxide together with inert gases may be formed, the so-called synthesis gas. The inert gases present in the synthesis gas as a rule originate from an air supply to the plant the purpose of which is to improve the corrosion resistance of the plant. Before the synthesis gas is vented to the atmosphere, ammonia and carbon dioxide may be removed from it in a scrubber. This ammonia and carbon dioxide are preferably returned to the reactor via the high-pressure condenser. The urea synthesis solution is sent to the stripper, where the urea synthesis solution is stripped in countercurrent with one of the raw materials ($CO_2$ or $NH_3$) and/or heat. In the condenser the gases released in the stripper are then condensed in the carbamate stream from the scrubber and returned to the reactor, optionally by making use of an ejector. As condenser use can be made of a falling-film condenser or a submerged condenser as described in NL-A-8400839. The submerged condenser can be placed horizontally or vertically. It is also possible to use a so-called combined reactor, which combines the functions of reactor and condenser.

According to the invention gases leaving the high-pressure synthesis section are condensed in a medium-pressure condenser at a pressure of 0.5-12 MPa. The pressure in the medium-pressure condenser is preferably 1-7 MPa.

The gases leaving the high-pressure synthesis section can originate from the reactor and/or the stripper.

The medium-pressure condenser also receives a carbamate stream. This carbamate stream comes from the medium-pressure recovery section or the low-pressure recovery section of the urea plant. It is desirable for the pressure of the carbamate stream supplied from the recovery section to be lower than the pressure in the medium-pressure condenser, as a result of which this carbamate has a certain ammonia and carbon dioxide absorption capacity. This absorption capacity is higher when the carbamate comes from a lower pressure. For this reason the carbamate stream is preferably supplied from the low-pressure recovery section.

In the medium-pressure condenser the ammonia and carbon dioxide still present in the off-gases from the high-pressure synthesis section are condensed and subsequently at least a part of the condensate formed is supplied to the high-pressure condenser. A part of the condensate formed can also be returned to the high-pressure reactor. Preferably the formed condensate is fed in its entirety to the high-pressure condenser.

If the high-pressure synthesis section comprises a scrubber, at least a part of the gases leave the high-pressure synthesis section via the high-pressure scrubber. These gases can be condensed in the medium-pressure condenser. When the high-pressure synthesis section comprises a scrubber at least a part of the formed condensate is fed to the high-pressure scrubber and from there to the high-pressure condenser. The formed condensate can also in part be returned to the high-pressure condenser and/or the high-pressure reactor.

Preferably the formed condensate is fed In its entirety to the high-pressure scrubber.

The carbamate in the formed condensate may crystallize out. This depends for instance on the pressure, the temperature and on the amount of water in the carbamate stream. Preferably the temperature in the medium-pressure condenser therefore is between 70 and 140° C.; more preferably between 80 and 115° C.

The urea plant preferably comprises a high-pressure synthesis section and a low-pressure recovery section.

It is also possible, for further removal of ammonia and carbon dioxide from the off-gas stream, to absorb the gas stream leaving the medium-pressure condenser in a medium-pressure scrubber. If a medium-pressure scrubber is used, the carbamate stream is not supplied to the medium-pressure condenser but to the medium-pressure scrubber. The formed condensate is then discharged to the medium-pressure condenser, where it further serves as solvent for ammonia and carbon dioxide. If the medium-pressure scrubber is operated at virtually the same pressure as the medium-pressure condenser, then the carbamate stream can flow by gravity from the medium-pressure scrubber to the medium-pressure condenser. If the medium-pressure scrubber is operated at a lower pressure than the medium-pressure condenser, then a pump is needed to transport the carbamate stream from the medium-pressure scrubber to the medium-pressure condenser.

The invention also relates to a urea plant containing a high-pressure synthesis section and one or more recovery section(s); the high-pressure synthesis section comprising a reactor, a stripper and a condenser, with the urea plant containing a medium-pressure condenser, which is connected to a gas outlet of the high-pressure synthesis section.

If the high-pressure synthesis section of the urea plant also comprises a scrubber, the medium-pressure condenser can be connected to the gas outlet of the high-pressure scrubber. The medium-pressure condenser can also be connected to the gas outlet of the stripper.

The urea plant may also contain a medium-pressure scrubber, which is connected to the gas outlet of the medium-pressure condenser.

The invention further also relates to a process for optimization of a urea plant that contains a high-pressure synthesis section and one or more recovery section(s), the high-pressure synthesis section comprising a reactor, a stripper, a condenser and optionally a scrubber, with a medium-pressure condenser being added to the urea plant in which gases coming from the high-pressure synthesis section are condensed, and the capacity of the high-pressure stripper being increased.

The capacity of the high-pressure stripper can for instance be increased by additionally Installing an extra stripper or by enlarging the existing stripper.

During the optimization also a medium-pressure scrubber can additionally be installed in which the gases coming from the medium-pressure condenser are absorbed.

The invention will below be elucidated by means of examples, without however being restricted thereto.

FIG. 1 shows a blockwise representation of a urea synthesis accrding to the state of the art (the Stamicarbon $CO_2$ stripping process). Urea synthesis solution is supplied to the high-pressure stripper (ST) from the high-pressure reactor (R). In addition, carbon dioxide (g) is supplied to the high-pressure stripper. In the stripper, unconverted carbamate is dissociated by means of heat and carbon dioxide as propellant to form ammonia and carbon dioxide gas. The carbon dioxide supplied contains air that is needed to protect the materials in the high-pressure synthesis section against corrosion.

The stripped urea solution (U) is transported to the subsequent low-pressure recovery section where further purification takes place.

The off-gases from the high-pressure stripper are sent to the high-pressure condenser (HPCC), together with the ammonia feed, via a high-pressure ejector (E). In the high-pressure condenser the exothermic carbamate reaction of ammonia and carbon dioxide yielding ammonium carbamate takes place. The heat released in this reaction is used to generate saturated steam having a pressure between 0.4 and 0.5 MPa. The pressure in the high-pressure synthesis section is controlled by means of the degree of condensation taking place in the high-pressure condenser. The formed carbamate and the unreacted ammonia and carbon dioxide are sent to the high-pressure reactor (R) where the endothermic urea reaction takes place. The off-gas stream from this high-pressure reactor goes to the high-pressure scrubber (SC) where by far the greater part of the ammonia and carbon dioxide still present in the off-gas is condensed by means of cooling water. The carbamate stream formed in the low-pressure recovery section (LP) is added to this high-pressure scrubber as solvent and/or absorbent in order to purify the inert stream from ammonia and carbon dioxide. In a downstream absorber (A) operating at a significantly lower pressure than the synthesis pressure further purification of these inert gases takes place. As a rule, ammonia water and/or steam condensate is used as absorbent in this absorber. The carbamate formed in the high-pressure scrubber is drawn in by the high-pressure ejector (E) and transported to the high-pressure carbamate condenser together with the ammonia feed.

Figure 2:
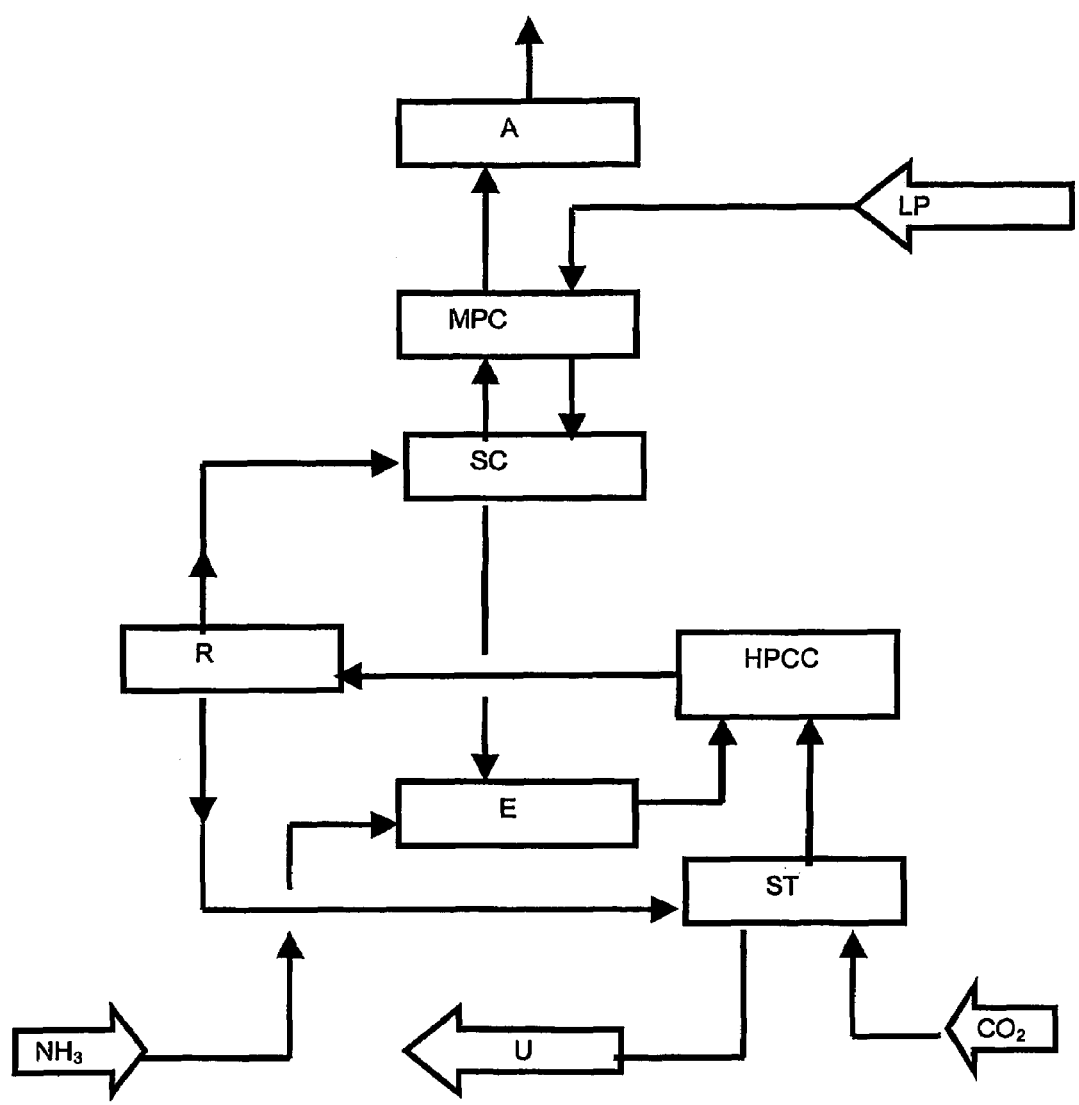

FIG. 2 represents a process for the preparation of urea according to the invention. Here, too, the urea synthesis solution leaving the reactor (R) is supplied to the high-pressure stripper (ST). In a similar way as described for FIG. 1, the urea synthesis solution in the high-pressure stripper is purified from the non-converted carbamate. The off-gases from this high-pressure stripper are supplied to the high-pressure condenser (HPCC), where the exothermic carbamate reaction takes place. In contrast to the process according to FIG. 1, the pressure of the formed saturated steam is now controlled at a value between 0.35 and 0.55 MPa. The formed carbamate together with the unreacted ammonia and carbon dioxide are sent to the high-pressure reactor (R) for the conversion into urea. The off-gas from this high-pressure reactor contains more ammonia and carbon dioxide than according to the state-of-the-art process as described in FIG. 1 and is supplied to the high-pressure scrubber (SC). In this scrubber the ammonia and carbon dioxide are condensed by means of cooling water. The off-gases from the high-pressure scrubber are directed to the newly installed medium-pressure condenser (MPC). In this process the pressure in the high-pressure synthesis section is controlled by increasing or decreasing the off-gas stream from the high-pressure scrubber that is allowed to pass through to the medium-pressure condenser. In the medium-pressure condenser the ammonia and carbon dioxide in the inert stream is condensed and the heat released is given off to the cooling water. The carbamate stream formed in the low-pressure recovery section (LP) is used as solvent and/or absorbent. The condensate formed in thsi medium-pressure condenser is pumped to the high-pressure scrubber (SC). This formed carbamate is used as solvent and/or absorbent in the high-pressure scrubber.

The inert stream leaving the medium-pressure condenser is purified in an absorber (A) in a similar way to that according to FIG. 1. The carbamate formed in the high-pressure scrubber is drawn in by the high-pressure ejector (E) and transported to the high-pressure carbamate condenser (HPCC) together with the ammonia feed.

Figure 3:
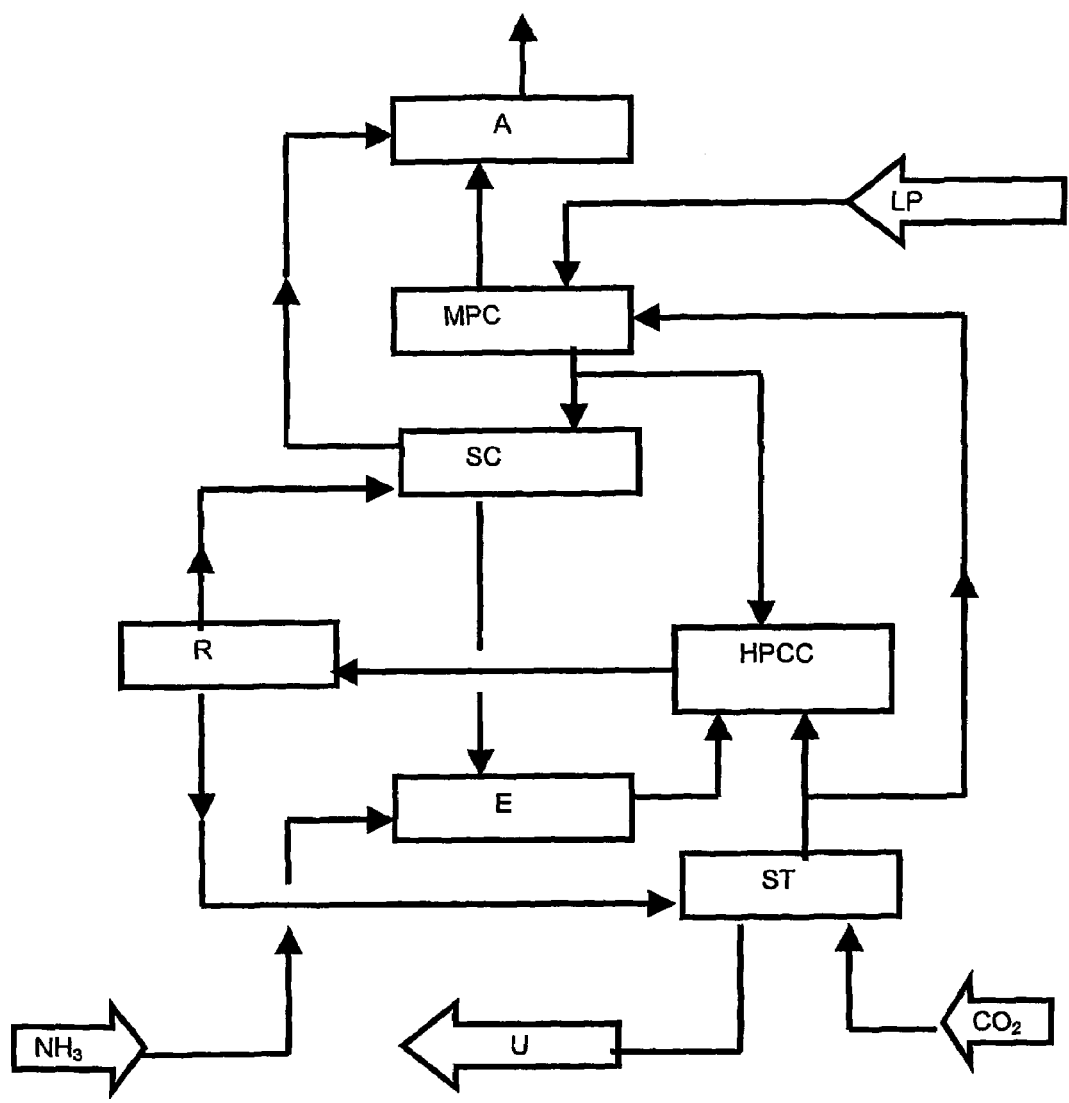

FIG. 3 also represents a process for the preparation of urea according to the invention. The urea synthesis solution leaving the reactor (R) is supplied to the high-pressure stripper (ST). In a similar way as described for FIG. 1, the urea synthesis solution in the high-pressure stripper is purified from the non-converted carbamate. The off-gases from this high-pressure stripper are partly supplied to the high-pressure condenser (HPCC) and partly to the newly installed medium-pressure condenser (MPC). In contrast to the process according to FIG. 1, the pressure of the saturated steam formed in the HPCC is now controlled at a value between 0.35 and 0.55 MPa. The formed carbamate together with the unreacted ammonia and carbon dioxide are sent to the high-pressure reactor (R) for the conversion into urea. The off-gas from this high-pressure reactor contains more ammonia and carbon dioxide than according to the state-of-the-art process as described in FIG. 1 and is supplied to the high-pressure scrubber (SC). In this scrubber the ammonia and carbon dioxide are condensed by means of cooling water. In this process the pressure in the high-pressure synthesis section is controlled by increasing or decreasing the off-gas stream from the high-pressure stripper that is allowed to pass through to the medium-pressure condenser. In the medium-pressure condenser the ammonia and carbon dioxide are condensed and the heat released is given off to the cooling water. The carbamate stream formed in the low-pressure recovery section (LP) is used as solvent and/or absorbent. The condensate formed in this medium-pressure condenser is pumped partly to the high-pressure scrubber (SC) and partly to the high-pressure condenser (HPCC). This formed carbamate is used as solvent and/or absorbent in the high-pressure scrubber. The off-gases from the high-pressure scrubber are purified in an absorber (A) functioning in a similar way to the absorber according to FIG. 1. The carbamate formed in the high-pressure scrubber is drawn in by the high-pressure ejector (E) and transported to the high-pressure carbamate condenser (HPCC) together with the ammonia feed.

The invention claimed is:

1. Process for the preparation of urea from ammonia and carbon dioxide in a urea plant that contains a high-pressure synthesis section and one or more recovery section(s) at a lower pressure, the high-pressure synthesis section comprising a reactor, a stripper and a condenser, characterized in that gases leaving the high-pressure synthesis section are condensed in a medium-pressure condenser at 0.5 -12 MPa to which also a carbamate stream from one of the recovery sections is supplied, after which at least a part of the formed condensate is supplied to the high-pressure condenser.

2. Process according to claim 1, characterized in that the formed condensate is also partly returned to the high-pressure reactor.

3. Process according to claim 1, characterized in that the formed condensate is supplied in its entirety to the high-pressure condenser.

4. Process according to claim 1, in which the high-pressure synthesis section also comprises a scrubber, characterized in that gases leaving the high-pressure synthesis section are condensed in a medium-pressure condenser to which also a carbamate stream from one of the recovery sections is supplied, after which at least a part of the formed condensate is supplied to the high-pressure scrubber and from there to the high-pressure condenser.

5. Process according to claim 4, characterized in that the formed condensate is also partly returned to the high-pressure condenser and/or the high-pressure reactor.

6. Process according to claim 4, characterized in that the formed condensate is supplied in its entirety to the high-pressure scrubber.

7. Process according to claim 1, characterized in that the temperature in the medium-pressure condenser is between 70 and 140° C.

8. Process according to claim 1, characterized in that the carbamate supplied to the medium-pressure condenser comes from the low-pressure recovery section of a urea plant.

9. Process according to claim 4, characterized in that the urea plant comprises a high-pressure synthesis section and a low-pressure recovery section.

10. Process according to claim 1, characterized in that the gas stream leaving the medium-pressure condenser is condensed in a medium-pressure scrubber at a pressure of 0.5-12 MPa to which a carbamate stream from one of the recovery section(s) of a urea plant is supplied, after which at least a part of the formed condensate is supplied to the medium-pressure condenser.

11. Urea plant containing a high-pressure synthesis section and one or more recovery section(s), the high-pressure synthesis section comprising a reactor, a stripper and a condenser, characterized in that the urea plant contains a medium-pressure condenser, which is connected to a gas outlet of the high-pressure synthesis section.

12. Urea plant according to claim 11, in which the high-pressure synthesis section also comprises a scrubber, characterized in that the medium-pressure condenser is connected to the gas outlet of the high-pressure scrubber.

13. Urea plant according to claim 11, characterized in that the urea plant also contains a medium-pressure scrubber, which is connected to the gas outlet of the medium-pressure condenser.

14. Process for optimization of a urea plant that contains a high-pressure synthesis section and one or more recovery section(s), the high-pressure synthesis section comprising a reactor, a stripper, a condenser and optionally a scrubber, characterized in that a medium-pressure condenser is added to the urea plant in which gases coming from the high-pressure synthesis section are condensed, and the capacity of the high-pressure stripper is increased.

15. Process according to claim 14, characterized in that the capacity of the high- pressure stripper is increased by additionally installing an extra stripper.

16. Process according to claim 14, characterized in that also a medium- pressure scrubber is additionally installed, in which the gases from the medium-pressure condenser are absorbed.

* * * * *